(12) United States Patent
Harder et al.

(10) Patent No.: US 9,095,642 B2
(45) Date of Patent: Aug. 4, 2015

(54) IMPLANT FOR RELEASING AN ACTIVE SUBSTANCE INTO A VESSEL THROUGH WHICH A BODY MEDIUM FLOWS

(75) Inventors: Claus Harder, Uttenreuth (DE); Roland Rohde, Burgdorf (DE); Bernd Heublein, Hannover (DE); Eva Heublein, legal representative, Coburg (DE); Nora Heublein, legal representative, Cologne (DE); Christoph Heublein, legal representative, Hannover (DE); Erhard Flach, Berlin (DE); Wolfgang Geistert, Rheinfelden (DE); Gernot Kolberg, Berlin (DE); Heinz Müller, Erlangen (DE)

(73) Assignee: BIOTRONIK VI Patent AG, Baar (CH)

(*) Notice: Subject to any disclaimer, the term of this patent is extended or adjusted under 35 U.S.C. 154(b) by 2253 days.

(21) Appl. No.: 10/597,099

(22) PCT Filed: Feb. 4, 2005

(86) PCT No.: PCT/EP2005/001167
§ 371 (c)(1),
(2), (4) Date: Apr. 9, 2008

(87) PCT Pub. No.: WO2005/075005
PCT Pub. Date: Jun. 18, 2005

(65) Prior Publication Data
US 2009/0182290 A1 Jul. 16, 2009

(30) Foreign Application Priority Data

Feb. 6, 2004 (DE) .................. 10 2004 006 745
Jun. 9, 2004 (DE) .................. 10 2004 029 611

(51) Int. Cl.
| | | |
|---|---|---|
| A61M 31/00 | (2006.01) |
| A61L 31/02 | (2006.01) |
| A61L 31/08 | (2006.01) |
| A61L 31/14 | (2006.01) |
| A61L 31/16 | (2006.01) |
| A61F 2/86 | (2013.01) |

(52) U.S. Cl.
CPC ............ *A61L 31/022* (2013.01); *A61L 31/08* (2013.01); *A61L 31/148* (2013.01); *A61L 31/16* (2013.01);
(Continued)

(58) Field of Classification Search
CPC ............. A61F 2210/0004; A61F 2250/0068; A61F 2/86; A61L 2300/604; A61L 31/022; A61L 31/08; A61L 31/148; A61L 31/16
USPC .......... 604/285, 286, 288; 623/1.42; 424/426, 424/423
See application file for complete search history.

(56) References Cited

U.S. PATENT DOCUMENTS

| | | | |
|---|---|---|---|
| 5,419,760 A | 5/1995 | Narciso, Jr. | |
| 5,824,049 A * | 10/1998 | Ragheb et al. | ............... 623/1.44 |

(Continued)

FOREIGN PATENT DOCUMENTS

| | | |
|---|---|---|
| DE | 19731021 A1 | 1/1999 |
| DE | 19945049 A1 | 3/2001 |
| DE | 10163106 A1 | 7/2003 |
| DE | 10237571 A1 | 2/2004 |
| DE | 10253634 A1 | 5/2004 |

(Continued)

*Primary Examiner* — Kami A Bosworth
*Assistant Examiner* — Imani Hayman
(74) *Attorney, Agent, or Firm* — Greer, Burns & Crain, Ltd.

(57) ABSTRACT

An implant for releasing an active substance into a vessel through which a body medium flows. The implant release an active substance into a vessel through which a body medium flows downstream from the location of the implant. A base of a biodegradable material is a carrier of the active substance to be released. The body medium flows past the implant and the active substance is release. The implant is configured so that the active substance does not contact a vessel wall at the location of implant.

16 Claims, 3 Drawing Sheets

(52) U.S. Cl.
CPC .......... *A61F 2/86* (2013.01); *A61F 2210/0004* (2013.01); *A61F 2250/0068* (2013.01); *A61L 2300/604* (2013.01)

(56) References Cited

U.S. PATENT DOCUMENTS

| | | | |
|---|---|---|---|
| 6,287,332 | B1 | 9/2001 | Bolz et al. |
| 2003/0139801 | A1* | 7/2003 | Sirhan et al. ................ 623/1.15 |
| 2004/0093062 | A1* | 5/2004 | Glastra ........................ 623/1.11 |
| 2005/0027350 | A1* | 2/2005 | Momma et al. .............. 623/1.42 |

FOREIGN PATENT DOCUMENTS

| | | |
|---|---|---|
| EP | 0 604 022 A1 | 6/1994 |
| EP | 0 875 218 B1 | 11/1998 |
| EP | 1270023 B1 | 1/2003 |
| EP | 1 310 266 A1 | 5/2003 |
| EP | 1389472 A2 | 2/2004 |
| EP | 1419793 B1 | 5/2004 |
| WO | WO 02/26109 A2 | 4/2002 |
| WO | WO 02/100452 A1 | 12/2002 |
| WO | WO 02100452 A1 * | 12/2002 |

* cited by examiner

IMPLANT FOR RELEASING AN ACTIVE SUBSTANCE INTO A VESSEL THROUGH WHICH A BODY MEDIUM FLOWS

PRIORITY CLAIM

This patent application is the U.S. National Phase of International Application No. PCT/EP2005/001167, having an International Filing Date of Feb. 4, 2005, which claims priority to German Patent Application No. DE 102004006745.7, filed Feb. 6, 2004 and German Patent Application No. 102004029611.1, filed Jun. 9, 2004, the disclosures of which are incorporated herein by reference in their entirety.

FIELD OF THE INVENTION

The invention relates to an implant for the release of an active substance into a vessel through which a body medium flows, and applications of such an implant.

BACKGROUND OF THE INVENTION

For centuries man has attempted to accelerate the healing process of pathological processes and conditions and reduce the symptoms associated with disease by the targeted administration of pharmaceutically active substances. Besides the selection of and search for suitable active substances, one problem resides in making the active substance available at the desired site of treatment. In order to minimise the side effects associated with administration, the release of the active substance should, if possible, be limited exclusively to the site of treatment. Furthermore, it is necessary in most cases, in order to optimise the effect, to maintain a posology as accurately as possible, i.e., to keep the concentration of active substance within specific range limits at the site of treatment over a predeterminable period. Conventionally active substances are applied orally, subcutaneously, intravenously or rectally. The conventional systemic administration of medicines results in considerable complications, particularly in the case of local diseases, e.g., tumours.

For many years there have therefore been increasing efforts to introduce the active substance more specifically into the body of the patient to be treated. The term 'Local Drug Delivery' (LDD) has been established to describe an exclusively local treatment from an implant, i.e., elution of an active substance essentially only into the tissue immediately surrounding the implant. The site of treatment at which the active substance is to exert its pharmacological action therefore lies immediately adjacent to the site of implantation.

An important area of application for LDD systems therefore lies in the improvement in biocompatibility of permanent implants such as stents, cardiac pacemakers or orthopaedic prostheses. In particular, complications caused by the presence of the implant or by the implantation should be reduced or avoided here.

The basic concept behind an administration of active substances that deviates from the LDD systems descried above, which is also applied in this invention, is that of providing a more distinct spatial separation between the site of implantation and the site of treatment. In other words, the active substance released on the implant should not act directly (locally) but should only exert its action in a region of tissue spatially separate from the implant after introduction into the body. The term 'Regional Drug Delivery'—or briefly RDD—will be used in the following to describe this type of regional active substance administration.

In some symptoms, e.g., locally limited tumours, active substances can be administered via the vascular system of the tissue to be treated. For this purpose it is necessary to introduce the implant into a vessel that lies downstream from the treatment site. A state of the art approach consists, for example, in injecting into the vessel a polymeric matrix containing the active substance. The matrix is designed so that it is converted immediately after injection to a tough film which adheres to the vascular walls. This film containing the active substance gradually decomposes, releasing the active substance. However, it is very difficult in practice to achieve such a pinpoint injection into the vessel concerned, which may lead to further complications, due to formation of thrombi for example. Finally, a posology also depends on the thickness of the film, i.e., it is difficult to predict the release characteristic that actually exists.

SUMMARY OF THE INVENTION

The essential feature of this invention is to supply an implant for releasing an active substance in a vessel through which a body medium flows.

This feature is achieved by the implant with the features mentioned herein. The implant for releasing an active ingredient in a vessel through which a body medium flows is characterised in that it comprises, in one exemplary embodiment, a basic body that consists of a biodegradable material as a substrate for the active substance to be released, and around which a body medium is circulated on the inside and/or outside. In other words the body medium, particularly blood, flows as far as possible unobstructed through or around the implant after its implantation. The basic body of the implant serves as a substrate for the active substance which is eluted at least as far as possible into the body medium flowing past and is distributed to a subordinate treatment site. The basic body of the implant is degraded in the course of time.

The implant is therefore ideally suited for the purposes of regional drug distribution (RDD), particularly for the treatment of tumours. These applications of the implant are claimed separately.

Vessel within the meaning of the invention refers to the totality of the arterial and venous blood vessels, including the vessels of the end flow path (in the broader sense also the lymph vessels) which, together with the heart, form one functional unit. The implant according to the invention is designed to release the active substance in the body medium which flows through the vessel. The active substance is therefore fed from the release site to the actual site of action located further downstream. The implant must therefore be designed so that the active substance, preferably at least 80% by weight of the active substance used, is released inside the vessel and is entrained by the body medium. Release in the direction of the vascular wall must be avoided. According to the invention the regions which are in contact with a vascular wall after the implantation preferably do not therefore act as substrates of the active substance. For example, if the implant has a tubular contour which is supported with its outer wall on the vessel after implantation, no active substance comes into contact with the outer wall.

Basic body within the meaning of the invention is understood to be a structure of the implant which guarantees the mechanical integrity of the implant before biodegradation commences and which serves as a substrate for the active substance to be released or as a matrix containing the active substance.

If the body medium only flows through the basic body, it is preferably designed as a tubular basic body open on its end sides, which body rests with its outside on the vascular wall (when implanted). Because of the shaping adapted to the vascular cross-section, turbulences in the body medium are largely suppressed or at least reduced, so that these implant variants are particularly suitable for vessels with a high volumetric flow of body medium.

According to a second variant of the implant according to the invention the body medium flows both on the inside and outside through or around the basic body. For this purpose the basic body may be designed as a hollow body which has inlets and outlets aligned in the direction of flow. These hollow bodies, which are accessible to the body medium immediately or shortly after implantation, may, in particular, be of tubular, cylindrical or spherical design. To guarantee the relative position of the implant in the body, anchor elements that are at least largely biodegradable are provided which extend from the basic body to the vascular wall, and there serve as an anchorage.

The anchor elements may, for example, have a zigzag-shaped, hook- or scale-like contour. The anchor elements must be designed so that they guarantee that the implant is anchored at least during the period of release for 90% by weight, and in particular 95% by weight of the active substance. The use of anchor elements reduces the area of contact between the implant and the vascular wall, so that the area of possible endothelialisation is also limited. A specific design of the anchor elements is dependent, among other things, on the flow conditions prevailing at the site of implantation, the release behaviour of the active substance and the degradation characteristic of the basic body, so that the implant must be adapted individually to the particular application. In order to achieve this feature a person skilled in the art will be able to take as a basis the general information available on the rheology of vessels in the body,
the influence of material modification or choice of alloys, including their processing and coating, on the degradation behaviour of the biodegradable materials, and
the influence on the release behaviour of active substances as a function of its modification or incorporation in a matrix.

For production reasons the anchor elements are preferably formed from the same biodegradable material and are integrally connected to the basic body.

A third variant of the implant according to the invention provides that only the body medium flows through the basic body. In other words, the basic body displays a closed structure in which only the outer walls of the basic body come into contact with the body medium. The basic body is either of compact design or the inner walls of the basic body present in hollow basic bodies are only accessible as a result of biodegradation. Particularly conceivable are basic bodies with a reticulate, truncated or laminar basic pattern. The basic bodies of these implant variants may in turn be fixed in the vessel by means of the anchor elements described above.

A preferred variant of the closed structure described above provides that the basic body has a multilayer structure, from the outside to the inside. The active substance to be released is located between the respective layers. In the body the outer layer is first degraded and the active substance underneath it is released. The next layer is then degraded and the active substance underneath that layer is released, and so on.

According to a preferred design of the invention the basic body of the implant consists at least partially of a biodegradable magnesium, iron or tungsten alloy. In these alloys the named element represents a proportion of at least 50% by weight, in particular 70%, and in particular preference 80% by weight of the alloy. Of particular preference are also magnesium alloys of the type WE, particularly WE43, where rare earth metals and yttrium are allowed to the alloy. The alloys mentioned can be well processed technically, have ideal mechanical material properties for realising the implants according to the invention, and display favourable degradation behaviour in the living organism. Moreover, a positive physiological effect appears to take place on the surrounding tissue, particularly in the case of the magnesium alloys, during the biodegradation of the basic body.

Furthermore, preference is given to magnesium alloys which have a content of 1 and 30% by weight of lithium because of their expected high biocompatibility. Also preferred are magnesium alloys with a content of 0.1% by weight to 10% by weight of aluminium, and magnesium alloys with a content of 0.01% by weight to 2% by weight of zirconium, because of their processing, mechanical and degradation-relevant properties. The constituents of the magnesium alloy mentioned—namely rare earth metals (E), yttrium (W), lithium (L), aluminium (A) and zirconium (K)—may form part of the alloy in any combination, the standardised abbreviation of the alloy constituents being indicated in brackets according to the ASTM. For example, alloy compositions of the following type may be used: LWE, AL, LAE and LE, where the sequence of letters may also be permutated according to the alloy composition used. The magnesium alloy therefore preferably contains one or more alloy constituents of the group rare earth metals, yttrium, lithium, aluminium and zirconium.

The basic body of the implant is also preferably designed so that is able to assume a first non-expanded condition and a second expanded condition. To realise such structures the numerous stent designs of prior art may be resorted to, but it must be mentioned that this variant of implant according to the invention need not or should not perform a supporting function for the vascular wall. It is only necessary to ensure that the implant is anchored in the vessel, i.e., is not entrained by the constant current of the body medium. In terms of design there are therefore greater degrees of freedom than in the case of implants with a support function. For example, if the active substance forms part of a coating covering the basic body, the partial regions of the basic body facing the body medium should be designed with as large an area as possible and should be covered by the active substance. An endothelialisation, i.e., growing in of the implant, may be tolerated provided that the elution of the active substance is not impaired. If necessary, substances that act against each other must be counteracted, for example, by means of certain surface structures on the laminar side of the implant, or by coating by means of the endothelialisation process.

Preferably the implant according to the invention for releasing an active substance into a vessel through which a body medium flows is designed as follows:

The basic body has a coating which contains the active substance, at least in certain regions, on its sides facing the vessel,
the basic body has one or more cavities which contain the active substance and/or
the basic body has one or more hollow bodies which contain the active ingredient.

A first variant therefore provides that the basic body is coated at least partially with the active ingredient. Here the coating may consist of the active substance itself but also of a biodegradable matrix containing the active substance. For example, it is conceivable for the active substance to be embedded in a matrix of hyaluronic acid or its derivatives. The choice of matrix, but also the form of administration of the active substance, greatly influences the in vivo release behaviour of the active substance. Because of the highly variable factors influencing the release behaviour, the release behaviour can only be optimised on the specific system. It should also be mentioned that the location of the coating must be preferably predetermined so that the active substance is discharged fully into the body medium flowing through the vessel and not in the direction of the adjacent vascular wall.

According to a second variant, cavities containing the active substance may be incorporated in the basic body. Cavities within the meaning of the invention refer to recesses, gaps or even drilled holes in the basic body of the implant which are not fully enclosed by the basic body, i.e., are accessible at least on one side. The active substance exists either in pure form or is incorporated in a matrix inside the cavity. The formation of such cavities is sufficiently well known, e.g. from the field of stents, and may be carried out by means of a laser process, for example. It remains to be stated merely that the body medium, through or around which the implant according to the invention flows gradually releases the active substance from the cavities. This process is accelerated as the degradation of the basic body progresses. Delayed release compared with coating may generally be expected.

Finally a further variant of the implant according to the invention provides that the basic body contains one or more hollow bodies into which the active substance is introduced. Here too the active substance may either be present as a pure substance or is embedded in a matrix. Cavities within the meaning of the invention are spaces which are totally enclosed by the basic body and into which the active ingredient has previously been introduced. The active substance only becomes available by the gradual degradation of the basic body and may dissolve in the body medium flowing past. Accordingly this variant generally displays the most delayed active substance release compared to both the variants described above. For example, a conceivable variant provides for the basic body to be formed from a hollow wire the inside of which is filled with the active substance.

All three of the previously mentioned variants can be combined in any manner, either to influence the release profile of an individual active substance or to control the release of different active substances in a time sequence that can be predetermined.

The implants can be introduced without problem with implant systems based on techniques of prior art into a vessel through a body medium flows. Provision may be made for the implant to be mounted on a balloon of a balloon catheter system. The catheter is then guided in a known manner as far as the implantation site. The balloon supporting the implant is the expanded and the implant positioned. After the balloon is deflated the catheter is withdrawn and the implant remains in a fixed position at the desired point until it is decomposed. For the purposes of introducing the implant according to the invention it may be advantageous for the implant to be able to assume a third, crimped condition on the substrate system.

An alternative implantation system to this may consist of a plurality of elongated nitinol wires, preferably three or four, which are expanded under a local thermal influence. The nitinol wires are arranged in relation to the implant so that the implant can be forced to be anchored at the implantation site by expansion of the same. The implantation system is therefore ideally suited for implants which incorporate the anchor elements described above.

BRIEF DESCRIPTION OF THE DRAWINGS

The invention is explained in greater detail in the following with reference to exemplary examples and the associated drawings, in which.

DETAILED DESCRIPTION OF THE EMBODIMENTS

Figure 1A:
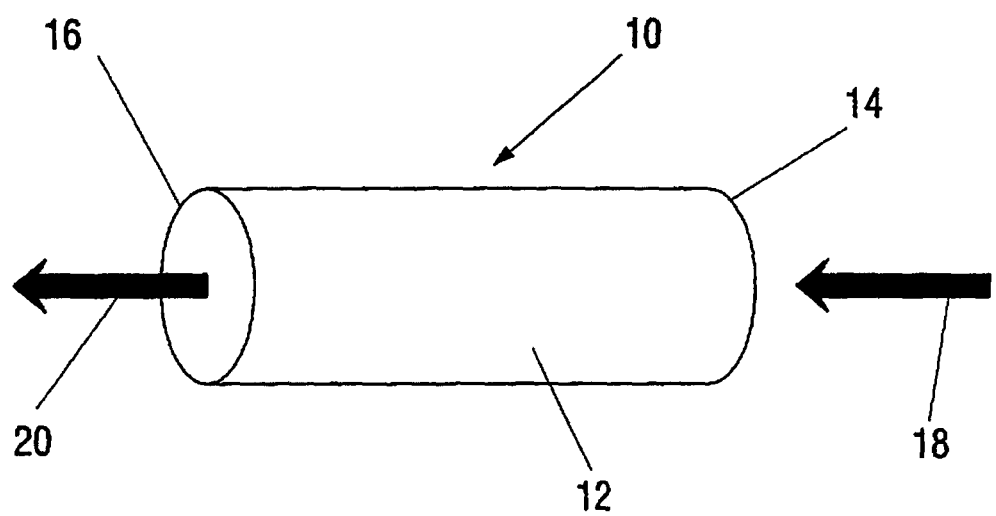
FIG. 1a shows a diagrammatic representation of implants according to the invention for the release of an active substance into a vessel through which a body medium flows.
Figure 1B:
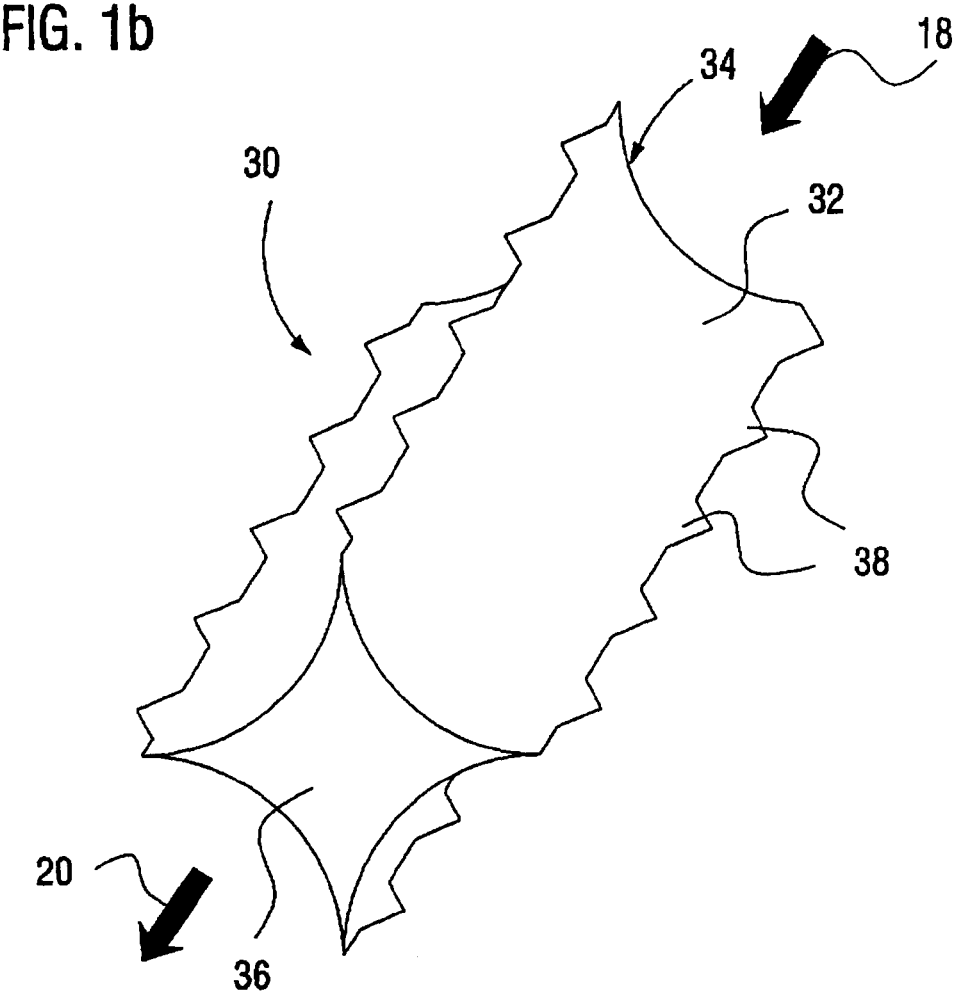
FIG. 1b shows a diagrammatic representation of implants according to the invention for the release of an active substance into a vessel through which a body medium flows.
Figure 1C:
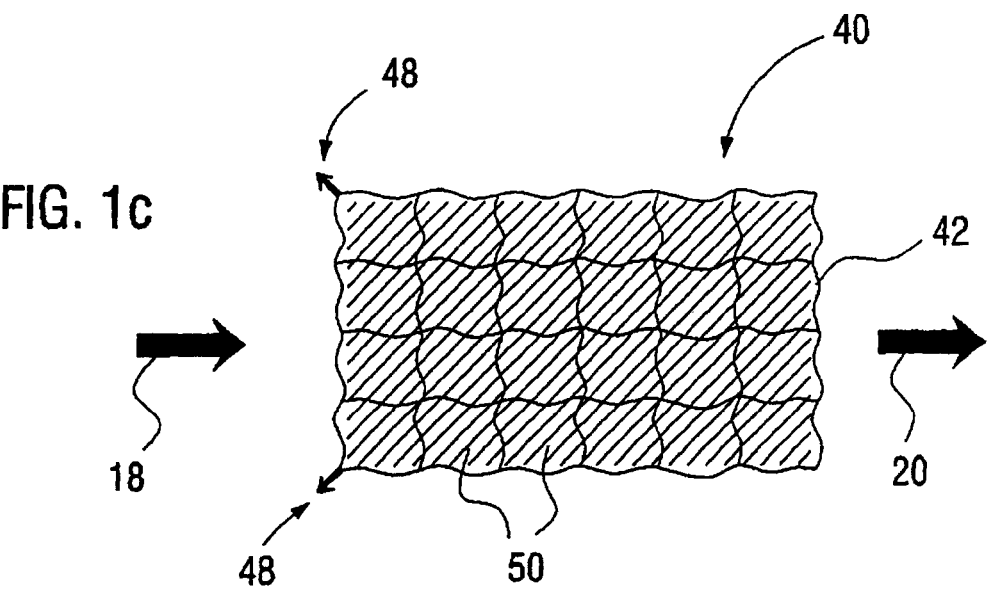
FIG. 1c shows a diagrammatic representation of implants according to the invention for the release of an active substance into a vessel through which a body medium flows.

FIGS. 1a to 1c show, in highly schematised fashion, implants 10, 30, 40 which are suitable for releasing active substances into a vessel through which a body medium flows.

FIG. 1a shows a first variant of an implant 10 according to the invention. Implant 10 consists of a tubular basic body 12 which is open on its front sides 14 and 16 and through which a body medium is able to flow. A direction of flow of the body medium flowing through basic body 12 of implant 10, particularly blood, is denoted by the two arrows 18, 20.

FIG. 1b shows a second variant of a suitable implant 30. Basic body 32 is designed as a hollow body, but is not adapted in its contour to the vessel in which implant 30 is to be anchored. In the direction of flow—again denoted by arrows 18, 20, the basic body has inlets and outlets 34, 36. In contrast to the variant shown in FIG. 1a, the body medium flows both on the inside and outside through or around basic body 32. For securing the relative position of implant 32 in the body, anchor elements 38 are arranged on the basic body, which elements are supported on the vascular wall after implantation and guarantee firm retention because of their shape. Anchor elements 38 are of zigzag design in this specific case, but may also assume other contours. Furthermore, anchor elements 38 consist at least as far as possible of a biodegradable material. Anchor elements 38 are designed so that anchoring of implant 30 is guaranteed at least during the period of release of 90% by weight, preferably 95% by weight, of the active substance. One specific design of anchor elements depends, among other things, on the flow conditions prevailing at the site of implantation, the release behaviour of the active ingredient and the degradation characteristic of basic body 32, so that implant 30 must be adapted individually to the particular application. For production reasons anchor elements 38 are preferably formed from the same biodegradable material as basic body 32, and are integrally connected to the same.

FIG. 1c shows diagrammatically a third variant of implant 40 according to the invention. According to this variant basic body 42 is designed as a closed structure, i.e., only the outer walls of the basic body come into contact with the body medium immediately after implantation. Basic body 42 shown has a reticulate structure and is fixed in the vessel by means of anchor elements 48. Clearances 50 formed between the individual threads of the net are spanned by a film-like matrix which contains the active substance. The matrix may, for example, be applied by immersing the reticulate basic body 42 in a solution containing the matrix, then drying the wetted basic body 42. Basic body 42, as well as the matrix, are formed from a biodegradable matrix.

Basic body 12, 32, 42 in FIGS. 1a, 1b and 1c, serves as a substrate for one, if necessary a plurality of active substances to be released in the body medium. During or at least after release of the active ingredient, basic body 12, 32, 42 decomposes as fully as possible, i.e., it consists at least as far as possible of a biodegradable material.

Alloys of the elements magnesium iron and tungsten in particular are considered as biodegradable material for basic body 12, 32, 42. In this case the elements mentioned each have proportions of the alloys of at least 60% by weight, preferably over 70% by weight and in particular preference over 80% by weight. Of particular preference are magnesium alloys which contain rare earth metals and yttrium, normally termed alloys of the type WE. Among the latter the material WEW43 has proved particularly suitable, i.e., the biodegradation of the active substance takes place in a controlled manner, the products of degradation released during the degradation have no, or at any rate little toxic effect, and conventional machining techniques for magnesium alloys may be used when processing the active substance.

Furthermore, magnesium alloys which have a content of 1 and 30% by weight of lithium are preferred because of their expected high biocompatibility. Preference is also given to magnesium alloys with a content of 0.1 to 10% by weight of aluminium, and magnesium alloys with a content of 0.01 to 2% by weight of zirconium, because of their processing, mechanical and degradation-relevant properties. The above-mentioned constituents of the magnesium alloy, namely are earth metals (E), yttrium (W), lithium (L), aluminium (A) and zirconium (K)—may form part of the alloy in any combination, the standardised abbreviation of the alloy constituents being indicated in brackets according to the ASTM. For example, alloy compositions of the following type may be used: LWE, AL, LAE and LE, where the sequence of letters may also be permutated according to the alloy composition used.

Basic body 12 of implant 10 is not shown in greater detail structurally in FIG. 1a. Normally, however, basic body 12 is not present as a fully closed tube but rather consists of a multiplicity of strut- or wire-like structural elements. Such a structure is particularly preferred because this greatly facilitates the introduction of the implant at the site of implantation. Thus when the structural elements are suitably designed, basic body 12 may have a first non-expanded condition that is smaller in diameter, and after widening at the site of implantation, it may have a second expanded condition. In the on-expanded condition of implant 10 the introduction of the implant as far as the site of implantation is understandably considerably facilitated. For this purpose provision may be made for implant 10 to be mounted on a balloon of a catheter system. The balloon catheter is then introduced into the body, as in the case of dilating stents in similar systems, and implant 10 is expanded by inflating the balloon at the desired point. For the purposes of introducing implant 10 it may be advantageous for implant 10 to be able to have a third, crimped condition on the substrate system. Furthermore, implantation systems operating with mechanical pulling or pushing devices, or by means of thermal deformations, may be used. For example, three or four elongated nitinol wires may be provided which expand under local thermal influence. The nitinol wires are arranged relative to the implant so that the implant is forced to be anchored at the implantation site due to the expansion of these wires. The implantation system is therefore ideally suited for implants which incorporate anchor elements 38, 48 described above.

In principle the design of the structural elements of an implant 10 forming basic body 12, according to FIG. 1a, may be based on stent designs of prior art. However, it must be stated that implant 10 need not perform a supporting function, i.e., the sent should have a very soft design to prevent vascular injuries. The design serves as an anchorage in the vessel and should prevent entrainment implant 10 by the body medium. The elution of the active substance should not be obstructed by the fact that implant 10 grows into the vascular wall, e.g. by surface modifications or the application of coatings with anti-proliferative substances at points on implant 10 which are in contact with the vascular wall.

Figure 2A:
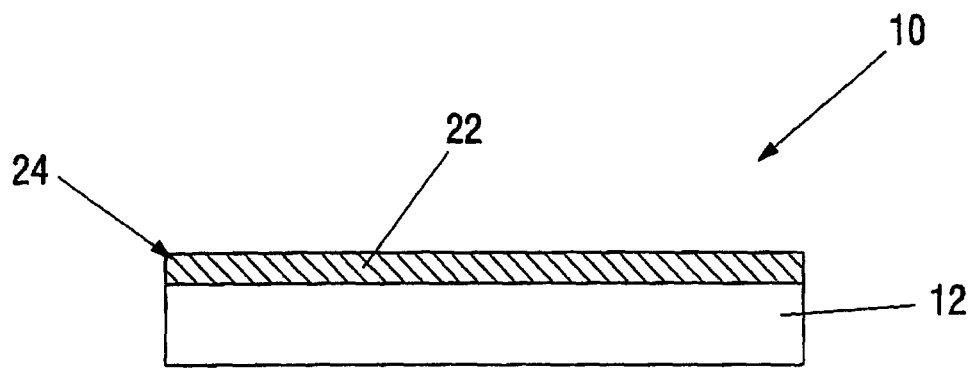
FIG. 2a shows a diagrammatic sectional view through partial regions of an implant according to FIG. 1a, in different variants.
Figure 2B:
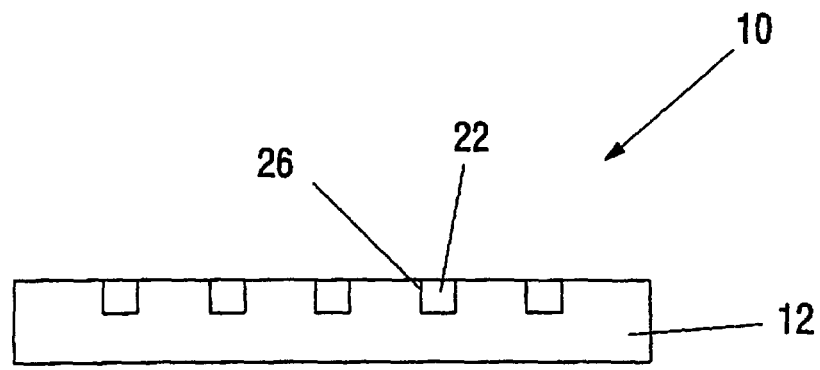
FIG. 2b shows a diagrammatic sectional view through partial regions of an implant according to FIG. 1b, in different variants.
Figure 2C:
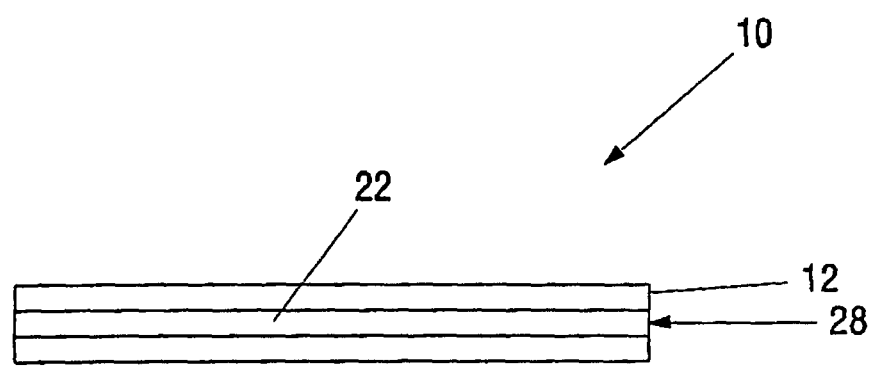
FIG. 2c shows a diagrammatic sectional view through partial regions of an implant according to FIG. 1c, in different variants.

FIGS. 2a to 2c show, in highly diagrammatic fashion, sections through implants 10, 30, 40 shown in FIGS. 1a to 1c, in a region in which basic body 12, 32, 42 acts as a substrate for active substance 22 or a matrix containing active substance 22. For the sake of simplicity reference is only made in the following to the variant of implant 10 shown in FIG. 1a. The measures indicated, however, can be transferred without difficulty to other implant variants with different shapes.

In FIG. 2a active substance 22 is applied to basic body 12 as a coating 24. Logically coating 24 lies on one inner side of tubular basic body 12, so that the flowing body medium can come into contact with active substance 22 and is able to elute it in dissolved form into the subordinate tissue regions. Active substance 22 may adhere to basic body 12 in pure form, e.g., as microcrystalline or amorphous product. However, it is also conceivable for active substance 22 to be embedded in a matrix in order to promote better adhesion to basic body 12, for example and/or to influence the release of active substance 22. For example, a biodegradable polymer, such as hyaluronic acid and its derivatives, may be considered as a matrix.

A second variant, shown in FIG. 2b, provides for the introduction of cavities 26 into basic body 12 of implant 10 and for them to be filled with active substance 22 or a matrix containing active substance 22. Such cavities 26 may be produced, for example, by means of laser processes of prior art. Cavities 26 can be realised in the form of gaps, holes or other geometries. Active substance 22 may be introduced into cavities 26, e.g., by immersing in a solution containing active substance 22, drying the solution and blowing off the active substance deposits present outside cavities 26. Because of the body medium flowing past, active substance 22 is slowly flushed out of cavities 26. At the same time this process is forced by the gradual degradation of basic body 12.

Finally, a third version of implant 10, shown in FIG. 2c, provides for basic body 12 to have a hollow space 28 into which active substance 22 is introduced. Not only the side of basic body 12 facing the body medium is degraded is active substance 22 eluted into the body medium. Such a system may, for example, be realised by the use of hollow wires into which solutions of active substance 22 have been introduced by capillary forces.

It is self-evident that the measures mentioned can be varied to control the release capacity of active substance 22. It is also conceivable for not only one active substance but a plurality of active substances to be released, offset in time relative to each other. The release of the active substance or substances depends in this case on the choice of substrate material, the geometric position of the active substance on the basic body (i.e., coating, cavity or hollow space), the properties of the matrix possibly containing the active substance and the rheological and anatomical conditions at the site of the implantation. The variants of the implant according to the invention described above are ideally suited for the purposes of regional drug delivery (RDD).

The invention claimed is:

1. An implant for releasing an active substance into a body vessel, the body vessel having a vessel wall and a vessel lumen through which body fluid can flow, the direction of fluid flow being defined by a vessel lumen axis, the implant comprising:
   a) a hollow member made at least partially of a biodegradable material and having a member wall with an interior surface defining a member lumen which is generally co-axial with the vessel lumen axis and through which fluid can flow, the member wall also having an exterior surface which can contact the vessel wall when implanted; and,
   b) at least one cavity defined within the interior surface of the member wall, each cavity having side wall portions and a bottom portion together defining a three-dimensional well with an opening exposed only to the member lumen axis and not exposed to the member wall exterior surface, the at least one cavity containing the active substance, the member wall interior surface portion not forming the cavity being substantially free of active substance, wherein active substance retained within the cavity is released over time and directed toward the vessel lumen axis and downstream from the member.

2. The implant of claim 1, wherein the hollow member comprises at least in part a biodegradable material selected from the group consisting of magnesium, iron and tungsten alloy.

3. The implant of claim 2, wherein the alloy is an alloy of the type WE.

4. The implant of claim 3, wherein the alloy is an alloy of the type WE43.

5. The implant of claim 2, wherein the alloy contains between 1 and 30% by weight of lithium.

6. The implant of claim 2, wherein the alloy contains between 0.1 and 10% by weight of aluminium.

7. The implant of claim 2, wherein the magnesium alloy contains between 0.01 and 2% by weight of zirconium.

8. The implant of claim 2, wherein the magnesium alloy comprises at least one constituent selected from the group consisting of rare earth metals, yttrium, lithium, aluminum and zirconium.

9. The implant of claim 1 wherein member has a first, non-expanded condition and a second, expanded condition.

10. The implant of claim 1, wherein the member is tubular, cylindrical, spherical or reticulate.

11. An implant for releasing an active substance into a body vessel, the body vessel having a vessel wall and a vessel lumen through which body fluid can flow, the direction of fluid flow being defined by a vessel lumen axis, the implant comprising:
   a) a hollow member made at least partially of a biodegradable material and having a wall with an interior surface defining a member lumen which is generally co-axial with the vessel lumen axis and through which fluid can flow, the wall also having an exterior surface which can contact the vessel wall when implanted; and,
   b) at least one hollow space containing the active substance and defined within the interior surface of the member, the hollow space in only the interior surface, wherein when the implant is implanted in the body vessel the top portion of the hollow space is degraded over time and the active substance retained within the hollow space is released through an opening created by the top portion toward and into the member lumen and is directed generally only toward the vessel lumen axis and downstream from the implant.

12. An implant for releasing an active substance into a body vessel, the body vessel having a vessel wall and a vessel lumen through which body fluid can flow, the direction of fluid flow being defined by a vessel lumen axis, the implant comprising:
   a basic body made at least partially of a biodegradable material configured to contact the vessel wall or anchor to the vessel wall and to be contained within the vessel lumen, the basic body further configured to allow the body fluid to flow along the lumen axis; and
   an active substance carried by said basic body in cavities or a hollow space of said basic body in a location of said basic body that prevents the active substance from contacting the vessel wall when said basic body is implanted in the body vessel, wherein said active substance is contained by a biodegradable portion of the basic body and located to be released into the body fluid to flow downstream of said basic body when the biodegradable portion biodegrades.

13. The implant of claim 12, wherein said biodegradable portion and said basic body permit at least 80% by weight of the active substance to be released into the body fluid.

14. The implant of claim 12, wherein said basic body is tubular and said active substance is only inside said basic body.

15. The implant of claim 12, wherein said basic body is a hollow with anchors on its outer side to anchor to the vessel wall with only the anchors contacting the vessel wall.

16. The implant of claim 15, wherein said basic body comprises a reticulate structure.

* * * * *